(12) United States Patent
Gossens et al.

(10) Patent No.: US 12,408,862 B2
(45) Date of Patent: Sep. 9, 2025

(54) DIGITAL BIOMARKER

(71) Applicant: Hoffmann-La Roche Inc., Little Falls, NJ (US)

(72) Inventors: Christian Gossens, Basel (CH); Michael Lindemann, Schopfheim (DE); Florian Lipsmeier, Basel (CH); Detlef Wolf, Grenzach-Wyhlen (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 888 days.

(21) Appl. No.: 17/553,754

(22) Filed: Dec. 16, 2021

(65) Prior Publication Data

US 2022/0104756 A1   Apr. 7, 2022

Related U.S. Application Data

(63) Continuation of application No. PCT/EP2020/066670, filed on Jun. 17, 2020.

(30) Foreign Application Priority Data

Jun. 19, 2019   (EP) ..................................... 19181332

(51) Int. Cl.
  *A61B 5/00* (2006.01)
  *G16H 40/63* (2018.01)
  *G16H 50/20* (2018.01)

(52) U.S. Cl.
  CPC .......... *A61B 5/4538* (2013.01); *A61B 5/0022* (2013.01); *A61B 5/4839* (2013.01);
  (Continued)

(58) Field of Classification Search
  CPC ... A61B 5/4538; A61B 5/0022; A61B 5/4839; A61B 5/6898; A61B 5/7275;
  (Continued)

(56) References Cited

U.S. PATENT DOCUMENTS 10,264,971 B1   4/2019   Kennedy
10,776,453 B2   9/2020   Fallon
(Continued)

FOREIGN PATENT DOCUMENTS

CN   104246781 A   12/2014
CN   107438398 A   12/2017
(Continued)

OTHER PUBLICATIONS

Bérard, C. et al., "A motor function measure for neuromuscular diseases. Construction and validation study" Neuromuscl Disord 15(7):463-470 (Jul. 1, 2005).

(Continued)

*Primary Examiner* — Jennifer Robertson
*Assistant Examiner* — Nidhi N Patel
(74) *Attorney, Agent, or Firm* — Thomas | Horstemeyer, LLP

(57) ABSTRACT

Currently, assessing the severity and progression of symptoms in a subject diagnosed with a muscular disability, in particular SMA involves in-clinic monitoring and testing of the subject every 6 to 12 months. However, monitoring and testing a subject more frequently is preferred, but increasing the frequency of in-clinic monitoring and testing can be costly and inconvenient to the subject. Thus, assessing the severity and progression of symptoms via remote monitoring and testing of the subject outside of a clinic environment as described herein provides advantages in cost, ease of monitoring and convenience to the subject. Systems, methods and devices according to the present disclosure provide a diagnostic for assessing of the axial motor function of a subject having a muscular disability, in particular SMA by active testing of the subject.

14 Claims, 5 Drawing Sheets

(52) U.S. Cl.
CPC .......... *A61B 5/6898* (2013.01); *A61B 5/7275* (2013.01); *G16H 40/63* (2018.01); *G16H 50/20* (2018.01)

(58) Field of Classification Search
CPC ... A61B 5/1124; A61B 5/1126; A61B 5/4566; A61B 5/4519; A61B 5/11; G16H 50/20; G16H 40/63
See application file for complete search history.

(56) References Cited

U.S. PATENT DOCUMENTS

| | | | |
|---|---|---|---|
| 2003/0043266 A1 | 3/2003 | Yoshikawa | |
| 2008/0286267 A1 | 11/2008 | Sing | |
| 2010/0169409 A1* | 7/2010 | Fallon | G16H 10/60 707/802 |
| 2011/0190594 A1 | 8/2011 | Heit | |
| 2013/0144190 A1 | 6/2013 | Bruce | |
| 2013/0209977 A1 | 8/2013 | Lathan | |
| 2013/0288777 A1 | 10/2013 | Short | |
| 2014/0100473 A1 | 4/2014 | O'Brien | |
| 2014/0163426 A1 | 6/2014 | Alberts | |
| 2014/0172442 A1 | 6/2014 | Broderick | |
| 2014/0247137 A1 | 9/2014 | Proud | |
| 2014/0295425 A1 | 10/2014 | Nagy | |
| 2014/0316220 A1 | 10/2014 | Sheldon | |
| 2014/0330159 A1 | 11/2014 | Costa | |
| 2014/0330172 A1 | 11/2014 | Jovanov | |
| 2015/0216448 A1 | 8/2015 | Lotan | |
| 2015/0220699 A1 | 8/2015 | Ostrovsky | |
| 2015/0351655 A1 | 12/2015 | Coleman | |
| 2016/0324487 A1 | 11/2016 | Guo | |
| 2016/0325057 A1 | 11/2016 | Morrison | |
| 2017/0055886 A1* | 3/2017 | Maples | A61B 5/1101 |
| 2018/0126219 A1 | 5/2018 | Parvaneh | |
| 2018/0296092 A1 | 10/2018 | Hassan | |
| 2019/0030396 A1 | 1/2019 | Karc | |
| 2019/0082771 A1 | 3/2019 | Shin | |
| 2019/0104970 A1 | 4/2019 | Cronin | |
| 2019/0111313 A1 | 4/2019 | Kalogris | |
| 2019/0167186 A1 | 6/2019 | Mlynczak | |
| 2019/0183383 A1 | 6/2019 | Brayanov | |
| 2019/0200915 A1 | 7/2019 | Baker | |
| 2019/0206566 A1 | 7/2019 | Lai | |
| 2019/0267003 A1 | 8/2019 | Khaleghi | |
| 2019/0380625 A1 | 12/2019 | Lindberg | |
| 2020/0000370 A1 | 1/2020 | Tao | |

FOREIGN PATENT DOCUMENTS

| | | |
|---|---|---|
| DE | 102009034002 A1 | 1/2011 |
| JP | 2015516957 A | 6/2015 |
| JP | 2015172820 A | 10/2015 |
| JP | 2017217052 A | 12/2017 |
| JP | 2018519133 A | 7/2018 |
| JP | 2018533605 A | 11/2018 |
| JP | 201933907 A | 3/2019 |
| JP | 2019514994 A | 6/2019 |
| JP | 201954988 A | 11/2019 |
| WO | 02069878 A2 | 9/2002 |
| WO | 2011/141734 A1 | 11/2011 |
| WO | 2013144803 A1 | 10/2013 |
| WO | 2013151938 A1 | 10/2013 |
| WO | 2013168364 A1 | 11/2013 |
| WO | 2015037089 A1 | 3/2015 |
| WO | 2016110804 A1 | 7/2016 |
| WO | 2016184935 A2 | 11/2016 |
| WO | 2017080967 A1 | 5/2017 |
| WO | 2017196874 A1 | 11/2017 |
| WO | 2018/050746 A1 | 3/2018 |
| WO | 2018/050763 A1 | 3/2018 |
| WO | 218050763 A1 | 3/2018 |
| WO | 2019/081640 A2 | 5/2019 |
| WO | 2019081640 A1 | 5/2019 |
| WO | 2019/122125 A1 | 6/2019 |

OTHER PUBLICATIONS

Bertini, E., et al., "Safety and efficacy of olesoxime in patients with type 2 or non-ambulatory type 3 spinal muscular atrophy: a randomised, double-blind, placebo-controlled phase 2 trial" Lancet Neurol 16(7):513-522 (Jul. 1, 2017).
Boukhvalova, A., et al., "Identifying and Quantifying Neurological Disability via Smartphone" Front Neurol 9(740):1-14 (Sep. 4, 2018).
Capelini, C., et al., "Improvements in motor tasks through the use of smartphone technology for individuals with Duchenne muscular dystrophy" Neuropsychiatr Dis Treat 13:2209-2217 (Aug. 18, 2017).
Chabanon, A., et al., "Prospective and longitudinal natural history study of patients with Type 2 and 3 spinal muscular atrophy: Baseline data NatHis-SMA study" PLOS ONE 13(7):e0201004 (1-28) (Jul. 26, 2018).
De Lattre, C., et al., "Motor function measure: validation of a short form for young children with neuromuscular diseases" Arch Phys Med Rehabil 94(11):2218-2226 (Nov. 1, 2013).
Fischer, D., et al., "Feasibility, reliability and convergent validity for digital biomarkers captured via a smartphone application (app) to assess motor behaviors in individuals with spinal muscular atrophy (SMA) in the JEWELFISH trial" Abstract (p. 190; vol. 29, Suppl. 1, S104; Neuromuscular Disorders) p. 1 ( Oct. 1, 2019).
"International Preliminary Report on Patentability—PCT/EP2020/066670" (Report Issuance Date: Dec. 21, 2021; Chapter I),:pp. 1-15 (Dec. 30, 2021).
"International Search Report—PCT/EP2020/066670" (w/Written Opinion),:pp. 1-20 (Sep. 3, 2020).
Lipsmeier, F., et al., "Evaluation of smartphone-based testing to generate exploratory outcome measures in a phase 1 Parkinson's disease clinical trial" MOV DISORD 33(8):1287-1297 (Aug. 1, 2018).
Ratni, H., et al., "Discovery of Risdiplam, a Selective Survival of Motor Neuron-2 (SMN2) Gene Splicing Modifier for the Treatment of Spinal Muscular Atrophy (SMA)" J Med Chem 61(15):6501-6517 (Jul. 25, 2018).
Servais, L., et al., "Innovative methods to assess upper limb strength and function in non-ambulant Duchenne patients" Neuromuscul Disord 23(2):139-148 (Feb. 1, 2013).
Shefner, J.M., "Strength Testing in Motor Neuron Diseases" Neurotherapeutics 14(1):154-160 (Jan. 1, 2017).
Vincent-Genod, D., et al., "Distal motor function assessments of children with spinal muscular atrophy: the use of a tablets as a part of the proposed kinect-MFM study" (Conference Abstract),:1 (May 1, 2018) https://hal.archives-ouvertes.fr/hal-01925906.
Chen et al. "Duet: exploring joint interactions on a smart phone and a smart watch.", 2014, In Proceedings of the SIGCHI Conference on Human Factors in Computing Systems (CHI '14). Association for Computing Machinery, New York, NY, USA, 159-168. https://doi.org/10.1145/2556288.2556955 (Year: 2014).
Chugai Pharmaceutical Co., Ltd. "European Medicines Agency Designated Risdiplam as a PRIME Medicine for the Treatment of Spinal Muscular Atrophy (SMA)" News Release, Dec. 17, 2018 (accessed Jul. 11, 2024) <URL: https://www.chugai-pharm.co.jp/news/detail/20181227163000_803.html>.
Del Rosario, Michael B., Stephen J. Redmond, and Nigel H. Lovell. 2015. "Tracking the Evolution of Smartphone Sensing for Monitoring Human Movement" Sensors 15, No. 8: 18901-18933. https://doi.org/10.3390/s150818901 (Year: 2015).
Japanese Office Action in related Japanese Application No. 2021-575286, mailed Mar. 31, 2025 (English Translation Provided).
"International Preliminary Report on Patentability with Written Opinion" for PCT/EP2020/066668 mailed Sep. 1, 2020.
International Search report—PCT/EP2020/066661 with Written Opinion, pp. 1-25, mailed Aug. 28, 2020.
"International Search Report—PCT/EP2020/066659" (w/Written Opinion),: 1-18 (Aug. 14, 2020).
International Search Report with Written Opinion for PCT /EP2020/066666 mailed Aug. 21, 2020, pp. 1-17.

(56) References Cited

OTHER PUBLICATIONS

Reus et al. "Objective evaluation of muscle strength in infants with hypotonia and muscle weakness" published by Science Direct, Apr. 2013, pp. 1-22 (Year: 2013).

Seferian, A., et al., "Upper Limb Evaluation and One-Year Follow up of Non-Ambulant Patients with Spinal Muscular Atrophy: An Observational Multicenter Teial" Plos One 10(4): 1-16 (Apr. 1, 2015).

Thap, T., et al., "High-Resolution Time-Frequency Spectrum-Based Lung Function Test from a Smartphone Microphone" SENSORS (Basel) 16(8): 1305 (1-16) (Aug. 17, 2016).

B. Wallace et al., "Detecting Cognitive Ability Changes in Patients With Moderate Dementia Using a Modified "Whack-a-Mole" Game," in IEEE Transactions on Instrumentation and Measurement, vol. 67, No. 7, pp. 1521-1534, Jul. 2018, doi: 10.1109/TIM .2017.2761638. (Year: 2018) A, et al.

Julayanont et al. The Montreal Cognitive Assessment (MoCA): Concept and Clinical Review Cognitive Screening Instruments: A Practical Approach. Springer-Verlag, pp. 111-152. 2012 (Year: 2012).

Alzheimer's Association, "Montreal Cognitive Assessment (MoCA)": 1-4 (2005) https ://www.alz.org/media/documents/short-moca-test.pdf.

Bachurin, S., et al. "Drugs in Clinical Trials for Alzheimer's Disease: The Major Trends"MED Res Rev 37 (5):1186-1225 (Sep. 1, 2017).

"International Preliminary Report on Patentability—PCT/EP2020/060185" (Report Issuance Date: Sep. 28, 2021, Chapter 1),: 1-10 (Sep. 28, 2021).

International Search Report—PCT/EP2020/060185 (w/Written Opinion), :pp. 1-15 (May 19, 2020).

Kaplan, E. et al. Boston Naming Test First edition, Philadelphia, PA-USA : Lea & Febiger,: 1-122 (Jan : 1, 1983).

Kourtis, L., et al., "Digital biomarkers for Alzheimer's disease: the mobile/ wearable devices. opportunity" NPJ Digit Med 2(9):1-9 (Feb. 21, 2019).

McRae, K., et al., "Semantic feature production norms for a large set of living and nonliving things" .Behav Res Methods 37(4):547-549 (Nov. 1, 2005).

Merlini, L., et al., "Reliability of hand-held dynamometry in spinal muscular atrophy" Muscle Nerve 26(1): 64-70 (Jul. 1, 2002).

\* cited by examiner

DIGITAL BIOMARKER

CROSS-REFERENCE TO RELATED APPLICATIONS

This application is a continuation of International Application No. PCT/EP2020/066670, filed Jun. 17, 2020, which claims priority to EP Application No. 19181332.8, filed Jun. 19, 2019, which are incorporated herein by reference in their entireties.

FIELD

Present invention relates to a medical device for improved subject testing and subject analysis. More specifically, aspects described herein provide diagnostic devices, systems and methods for assessing symptom severity and progression of a muscular disability, in particular spinal muscular atrophy (SMA) in a subject by active testing of the subject.

BACKGROUND

Spinal muscular atrophy (SMA) is an autosomal recessive disease also called proximal spinal muscular atrophy and 5q spinal muscular atrophy. It is a life-threatening, neuromuscular disorder with low prevalence associated with loss of motor neurons and progressive muscle wasting.

SMA has become a health problem and also a significant economic burden for health systems. Since SMA is a clinically heterogeneous disease of the CNS, diagnostic tools are needed that allow a reliable diagnosis and identification of the present disease status and symptom progression and can, thus, aid an accurate treatment.

There are several standardized methods and tests for measuring the symptom severity and progression in subjects diagnosed with SMA. The test involves a doctor measuring the subject's abilities to perform the physical function. These standardized tests can provide an assessment of the various symptoms, in particular axial motor function, and can help track changes in these symptoms over time. Assessing symptom severity and progression using standardized methods and tests can, therefore, help guide treatment and therapy options.

Currently, assessing the severity and progression of symptoms in a subject diagnosed with a muscular disability, in particular SMA, involves in-clinic monitoring and testing of the subject every 6 to 12 months (motor-function-measure-.org/user-s-manual.aspx, MFM-5, 15,32). While monitoring and testing a subject more frequently is ideal, increasing the frequency of in-clinic monitoring and testing can be costly and inconvenient to the subject.

BRIEF SUMMARY

The following presents a simplified summary of various aspects described herein. This summary is not an extensive overview, and is not intended to identify key or critical elements or to delineate the scope of the claims. The following summary merely presents some concepts in a simplified form as an introductory prelude to the more detailed description provided below. Aspects described herein describe specialized medical devices for assessing the severity and progression of symptoms for a subject diagnosed with a muscular disability, in particular SMA. Testing and monitoring may be done remotely and outside of a clinic environment, thereby providing lower cost, increased frequency, and simplified ease and convenience to the subject, resulting in improved detection of symptom progression, which in turn results in better treatment.

According to one aspect, the disclosure relates to a diagnostic device for assessing the axial motor function of a muscular disability, in particular SMA, in a subject. The device includes at least one processor, one or more sensors associated with the device, and memory storing computer-readable instructions that, when executed by the at least one processor, cause the device to receive a plurality of first sensor data via the one or more sensors associated with the device, extract, from the received first sensor data, a first plurality of features associated with the axial motor function of a muscular disability, in particular SMA, in the subject, and determine a first assessment of the axial motor function of a muscular disability, in particular SMA, based on the extracted first plurality of features.

Some embodiments are listed below:

E1 diagnostic device for assessing the axial motor function of a subject with a muscular disability, in particular SMA, the device comprising:
  at least one processor;
  one or more sensors associated with the device; and
  memory storing computer-readable instructions that, when executed by the at least one processor, cause the device to:
  receive a plurality of first sensor data via the one or more sensors associated with the device;
  extract, from the received first sensor data, a first plurality of features associated with the axial motor function of a subject with a muscular disability, in particular SMA; and
  determine a first assessment of the axial motor function of said subject based on the extracted first plurality of features.

E2 The device of E1, wherein the computer-readable instructions, when executed by the at least one processor, further cause the device to:
  prompt the subject to perform the diagnostic tasks of balancing on the rope for 30 s;
  in response to the subject performing the diagnostic tasks, receive a plurality of second sensor data via the one or more sensors associated with the device;
  extract, from the received second sensor data, a second plurality of features associated with the axial motor function of said subject; and
  determine a second assessment of the axial motor function of said subject based on the extracted second plurality of features.

E3 The device of any one of E1-E2, wherein the device is a smartphone.

E4 The device of any one of E1-E3, wherein the diagnostic tasks is associated with at least one of a motor function test.

E5 A computer-implemented method for assessing the axial motor function of a subject with a muscular disability, in particular SMA, the method comprising:
  receiving a plurality of first sensor data via one or more sensors associated with a device;
  extracting, from the received first sensor data, a first plurality of features associated with the axial motor function of a subject with a muscular disability, in particular SMA; and
  determining a first assessment of the axial motor function of a subject with a muscular disability, in particular SMA based on the extracted first plurality of features.

E6 The computer-implemented method of E5, further comprising:

prompting the subject to perform one or more diagnostic tasks;

in response to the subject performing the one or more diagnostics tasks, receiving, a plurality of second sensor data via the one or more sensors;

extracting, from the received second sensor data, a second plurality of features associated with the axial motor function of a subject with a muscular disability, in particular SMA; and determining a second assessment of the axial motor function of a subject with a muscular disability, in particular SMA based on at least the extracted second sensor data.

E7 The computer-implemented method of any one of E5-E6, whereby the subject's axial motor function is assessed based on an active task, in particular the balancing on the rope for 30 s.

E8 The device of any one of E1-E4 or the computer-implemented method of any one of E5-E7, wherein the subject is human.

E9 A non-transitory machine readable storage medium comprising machine-readable instructions for causing a processor to execute a method for assessing the axial motor function of a subject with a muscular disability, in particular SMA, the method comprising:

receiving a plurality of sensor data via one or more sensors associated with a device;

extracting, from the received sensor data, a plurality of features associated with the axial motor function of a subject with a muscular disability, in particular SMA; and determining an assessment of the axial motor function of a subject with a muscular disability, in particular SMA based on the extracted plurality of features.

E10 A method assessing a muscular disability, in particular SMA, in a subject comprising the steps of:

determining the usage behavior parameter from a dataset comprising usage data for a device according to any one of E1-E5 within a first predefined time window wherein said device has been used by the subject; and comparing the determined at least one usage behavior parameter to a reference, whereby a subject with a muscular disability, in particular SMA, will be assessed.

E11 A method of identifying a subject for having a subject with a muscular disability, in particular SMA, comprising i) scoring a subject on the diagnostic tasks of balancing on the rope for 30 s, ii) comparing the determined score to a reference, whereby a muscular disability, in particular SMA, will be assessed.

E12 The method of E11, further comprising administering a pharmaceutically active agent to the subject to decrease likelihood of progression of a muscular disability, in particular SMA, in particular wherein the pharmaceutically active agent is suitable to treat SMA in a subject, in particular a m7GpppX Diphosphatase (DCPS) Inhibitors, Survival Motor Neuron Protein 1 Modulators, SMN2 Expression Inhibitors, SMN2 Splicing Modulators, SMN2 Expression Enhancers, Survival Motor Neuron Protein 2 Modulators or SMN-AS1 (Long Non-Coding RNA derived from SMN1) Inhibitors, more particular Nusinersen, Onasemnogene abeparvovec, Risdiplam or Branaplam.

E13 A combination of the method according to E12, whereby a determined at least one parameter being better compared to the reference parameter of said patient before said subject received treatment with the pharmaceutical agent.

E14 A method according to E12-E13, whereby the subject is human.

E15 A method according to E12-E14, whereby the agent is Risdiplam.

BRIEF DESCRIPTION OF THE DRAWINGS

A more complete understanding of aspects described herein and the advantages thereof may be acquired by referring to the following description in consideration of the accompanying drawings, in which like reference numbers indicate like features, and wherein.

DETAILED DESCRIPTION

Figure 1:
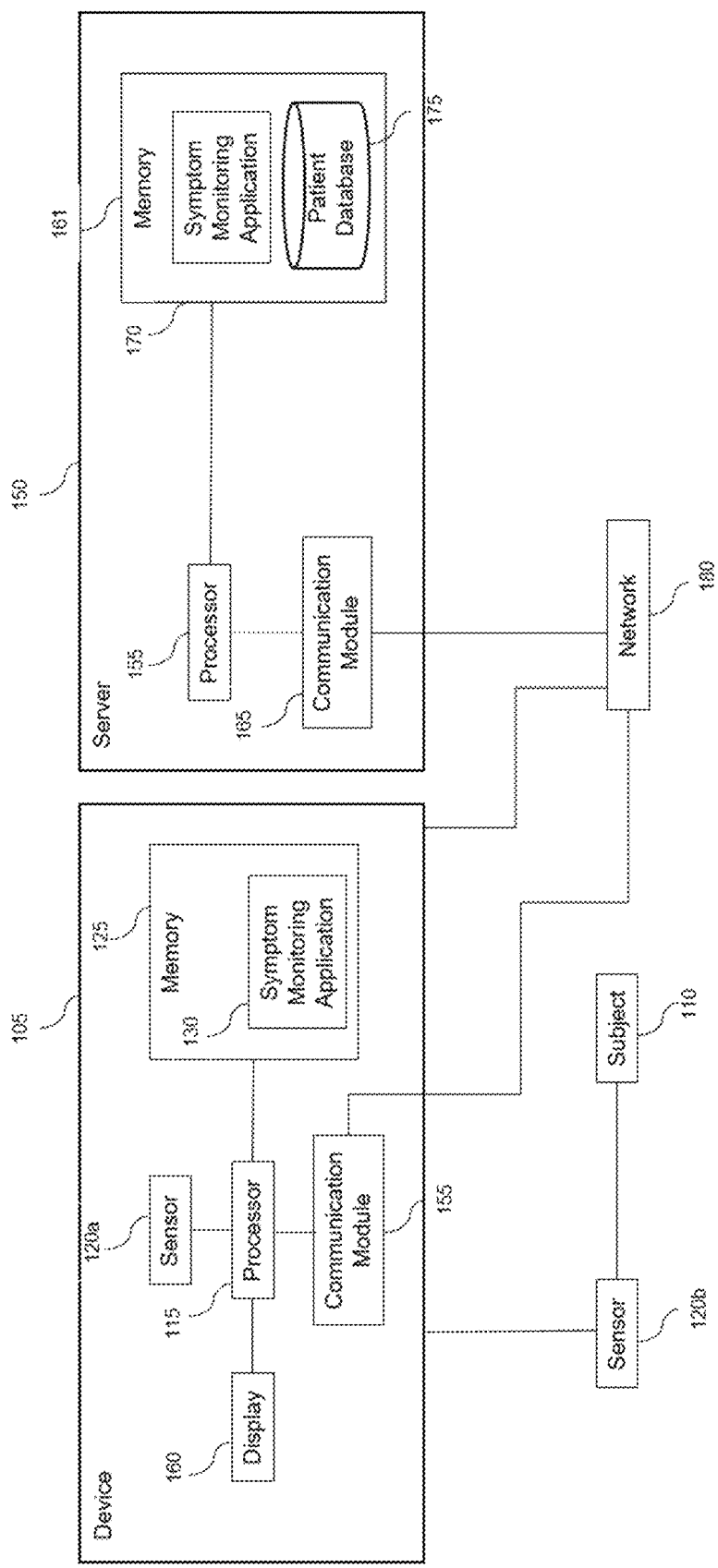
FIG. 1 is a diagram of an example environment in which a diagnostic device for assessing axial motor function of a muscular disability, in particular SMA, in a subject is provided according to an example embodiment.

In the following description of various aspects, reference is made to the accompanying drawings, which form a part hereof, and in which is shown by way of illustration various embodiments in which aspects described herein may be practiced. It is to be understood that other aspects and/or embodiments may be utilized and structural and functional modifications may be made without departing from the scope of the described aspects and embodiments. Aspects described herein are capable of other embodiments and of being practiced or being carried out in various ways. Also, it is to be understood that the phraseology and terminology used herein are for the purpose of description and should not be regarded as limiting. Rather, the phrases and terms used herein are to be given their broadest interpretation and meaning. The use of "including" and "comprising" and variations thereof is meant to encompass the items listed thereafter and equivalents thereof as well as additional items and equivalents thereof. The use of the terms "mounted," "connected," "coupled," "positioned," "engaged" and similar terms, is meant to include both direct and indirect mounting, connecting, coupling, positioning and engaging.

Systems, methods and devices described herein provide a diagnostic for assessing the axial motor function of a muscular disability, in particular SMA, in a subject. In some embodiments, the diagnostic may be provided to the subject as a software application installed on a mobile device, in particular a smartphone.

In some embodiments, the diagnostic obtains or receives sensor data from one or more sensors associated with the mobile device as the subject performs activities of daily life. In some embodiments, the sensors may be within the mobile device like a smartphone or wearable sensors like a smartwatch. In some embodiments, the sensor features associated with the symptoms of a muscular disability, in particular SMA, are extracted from the received or obtained sensor data. In some embodiments, the assessment of the symptom severity and progression of a muscular disability, in particular SMA, in the subject is determined based on the extracted sensor features.

In some embodiments, systems, methods and devices according to the present disclosure provide a diagnostic for assessing a muscular disability, in particular SMA, in a subject based on active testing of the subject. In some embodiments, the diagnostic prompts the subject to perform diagnostic tasks. In some embodiments, the diagnostic tasks are anchored in or modelled after established methods and standardized tests. In some embodiments, in response to the subject performing the diagnostic task, the diagnostic obtains or receives sensor data via one or more sensors. In some embodiments, the sensors may be within a mobile device or wearable sensors worn by the subject. In some embodiments, sensor features associated with the symptoms of a muscular disability, in particular SMA, are extracted from the received or obtained sensor data. In some embodiments, the assessment of the symptom severity and progression of a muscular disability, in particular SMA, in the subject is determined based on the extracted features of the sensor data.

Assessments of symptom severity and progression of a muscular disability, in particular SMA, using diagnostics according to the present disclosure correlate sufficiently with the assessments based on clinical results and may thus replace clinical subject monitoring and testing. Example diagnostics according to the present disclosure may be used in an out of clinic environment, and therefore have advantages in cost, ease of subject monitoring and convenience to the subject. This facilitates frequent, in particular daily, subject monitoring and testing, resulting in a better understanding of the disease stage and provides insights about the disease that are useful to both the clinical and research community. An example diagnostic according to the present disclosure can provide earlier detection of even small changes in the axial motor function of a muscular disability, in particular SMA, in a subject and can therefore be used for better disease management including individualized therapy.

According to the disclosed embodiments herein, sensors can be for example motion sensors, gyroscope sensors, position sensors or pressure sensors.

FIG. 1 is a diagram of an example environment in which a diagnostic device 105 is provided for assessing the axial motor function of a muscular disability, in particular SMA, in a subject 110. In some embodiments, the device 105 may be a smartphone, a smartwatch or other mobile computing device. The device 105 includes a display screen 160. In some embodiments, the display screen 160 may be a touchscreen. The device 105 includes at least one processor 115 and a memory 125 storing computer-instructions for a symptom monitoring application 130 that, when executed by the at least one processor 115, cause the device 105 to assess the axial motor function of a muscular disability, in particular SMA. The device 105 receives a plurality of sensor data via one or more sensors associated with the device 105. In some embodiments, the one or more sensors associated with the device is at least one of a sensor disposed within the device or a sensor worn by the subject and configured to communicate with the device. In FIG. 1, the sensors associated with the device 105 include a first sensor 120*a* that is disposed within the device 105 and a second sensor 120*b* that is disposed within another device configured to be worn by the subject 110. The device 105 receives a plurality of first sensor data via the first sensor 120*a* and a plurality of second sensor data via the second sensor 120*b* as the subject 110 performs activities.

The device 105 extracts, from the received first sensor data and second sensor data, features associated with the axial motor function of a muscular disability, in particular SMA, in the subject 110. In some embodiments, the symptoms of a muscular disability, in particular SMA, in the subject 110 may include a symptom indicative of an axial motor function of the subject 110, a symptom indicative of the axial motor function of the subject 110.

In some embodiments, the sensors 120 associated with the device 105 may include sensors associated with Bluetooth and WiFi functionality and the sensor data may include information associated with the Bluetooth and WiFi signals received by the sensors 120. In some embodiments, the device 105 extracts data corresponding to the density of Bluetooth and WiFi signals received or transmitted by the device 105 or sensors, from the received first sensor data and second sensor data. In some embodiments, an assessment of the axial motor function of the subject 110 may be based on the extracted Bluetooth and WiFi signal data (e.g., an assessment of subject sociability may be based in part on the density of Bluetooth and WiFi signals picked up).

The device 105 determines an assessment of the axial motor function of a muscular disability, in particular SMA, in the subject 110 based on the extracted features of the received first and second sensor data. In some embodiments, the device 105 send the extracted features over a network 180 to a server 150. The server 150 includes at least one processor 155 and a memory 161 storing computer-instructions for a symptom assessment application 170 that, when executed by the server processor 155, cause the processor 155 to determine an assessment of the axial motor function of a muscular disability, in particular SMA, in the subject 110 based on the extracted features received by the server 150 from the device 105. In some embodiments, the symptom assessment application 170 may determine an assessment of the axial motor function of a muscular disability, in particular SMA, in the subject 110 based on the extracted features of the sensor data received from the device 105 and a subject database 175 stored in the memory 160. In some embodiments, the subject database 175 may include subject and/or clinical data. In some embodiments, the subject database 175 may include in-clinic and sensor-based measures of the axial motor function at baseline and longitudinal from a muscular disability, in particular SMA, subjects. In some embodiments, the subject database 175 may be independent of the server 150. In some embodiments, the server 150 sends the determined assessment of the axial motor function of a muscular disability, in particular SMA, in the subject 110 to the device 105. In some embodiments, the device 105 may output the assessment of the axial motor function of a muscular disability, in particular SMA. In some embodiments, the device 105 may communicate information to the subject 110 based on the assessment. In some embodiments, the assessment of the axial motor function of a muscular disability, in particular SMA, may be communicated to a clinician that may determine individualized therapy for the subject 110 based on the assessment.

In some embodiments, the computer-instructions for the symptom monitoring application 130, when executed by the at least one processor 115, cause the device 105 to assess the axial motor function of a muscular disability, in particular SMA, in the subject 110 based on active testing of the subject 110. The device 105 prompts the subject 110 to perform one or more tasks. In some embodiments, prompting the subject to perform the one or more diagnostic tasks includes prompting the subject to transcribe pre-specified sentences or prompting the subject to perform one or more actions. In some embodiments, the diagnostic tasks are anchored in or modelled after well-established methods and standardized tests for evaluating and assessing a muscular disability, in particular SMA.

In response to the subject 110 performing the one or more diagnostic tasks, the diagnostic device 105 receives a plurality of sensor data via the one or more sensors associated with the device 105. As mentioned above, the sensors associated with the device 105 may include a first sensor 120a that is disposed within the device 105 and a second sensor 120b that is disposed within another device configured to be worn by the subject 110. The device 105 receives a plurality of first sensor data via the first sensor 120a and a plurality of second sensor data via the second sensor 120b. In some embodiments, the one or more diagnostic tasks may be associated with the axial motor function measurement, in particular measure of the duration and accuracy of drawing a shape when performing the task.

The device 105 extracts, from the received plurality of first sensor data and the received plurality of second sensor data, features associated with the axial motor function of a muscular disability, in particular SMA in the subject 110. The symptoms of a muscular disability, in particular SMA in the subject 110 may include a symptom indicative of the axial motor function of the subject 110.

The device 105 determines an assessment of the axial motor function of a muscular disability, in particular SMA in the subject 110 based on the extracted features of the received first and second sensor data. In some embodiments, the device 105 sends the extracted features over a network 180 to a server 150. The server 150 may include at least one processor 155 and a memory 161 storing computer-instructions for a symptom assessment application 170 that, when executed by the server processor 155, cause the processor 155 to determine an assessment of the axial motor function of a muscular disability, in particular SMA in the subject 110 based on the extracted features received by the server 150 from the device 105. In some embodiments, the symptom assessment application 170 may determine an assessment of the axial motor function of a muscular disability, in particular SMA in the subject 110 based on the extracted features of the sensor data received from the device 105 and a subject database 175 stored in the memory 160. In some embodiments, the subject database 175 may include subject and/or clinical data. In some embodiments, the subject database 175 may include measures of the axial motor function at baseline and longitudinal from a muscular disability, in particular SMA subjects. In some embodiments, the subject database 175 may include data from subjects at other stages of a muscular disability, in particular SMA. In some embodiments, the subject database 175 may be independent of the server 150. In some embodiments, the server 150 sends the determined assessment of the axial motor function of a muscular disability, in particular SMA in the subject 110 to the device 105. In some embodiments, the device 105 may output the assessment of the axial motor function of a muscular disability, in particular SMA. In some embodiments, the device 105 may communicate information to the subject 110 based on the assessment. In some embodiments, the assessment of the axial motor function of a muscular disability, in particular SMA may be communicated to a clinician that may determine individualized therapy for the subject 110 based on the assessment.

Figure 2:
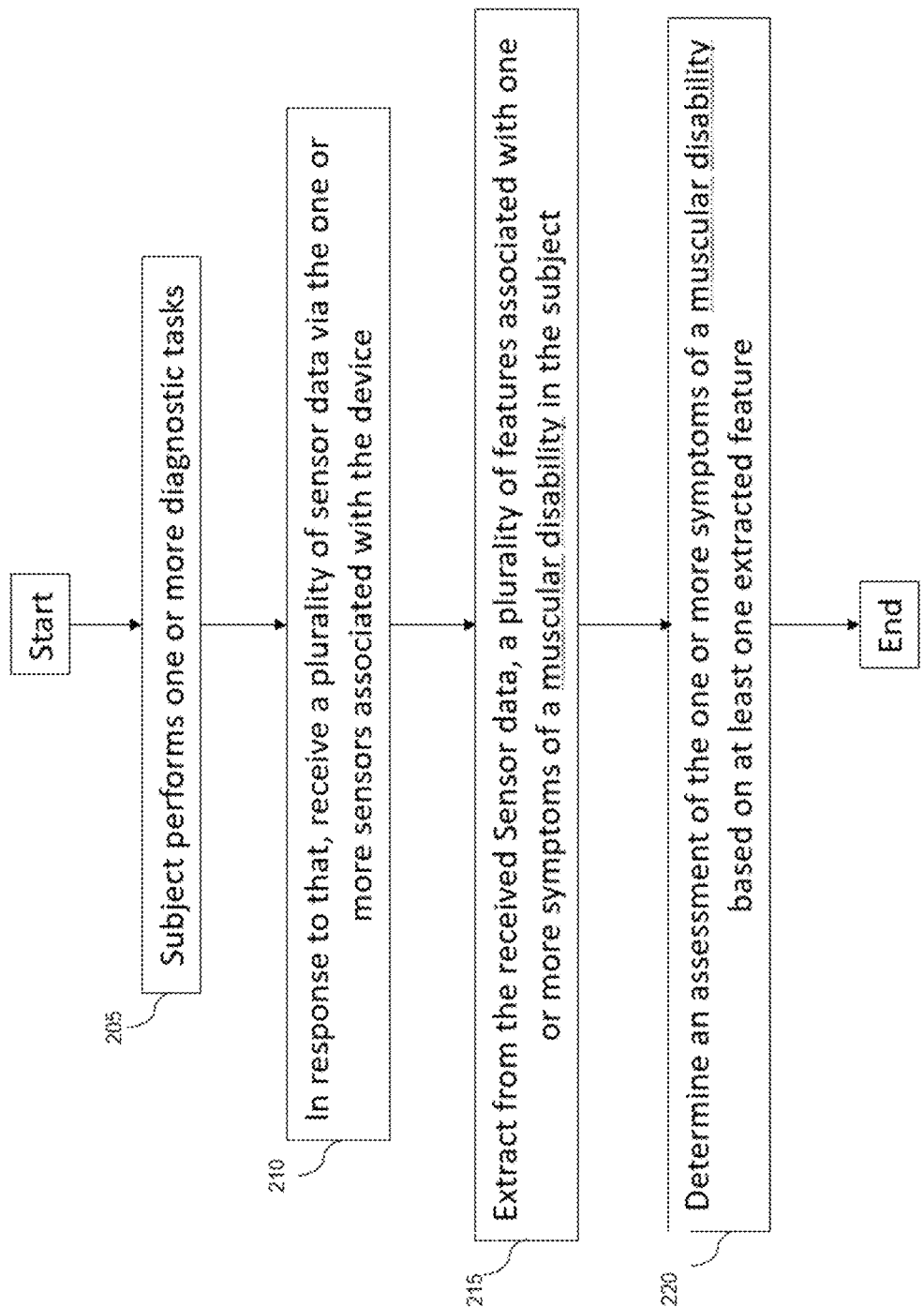
FIG. 2 is a flow diagram of a method for assessing the axial motor function of a muscular disability, in particular SMA, in a subject based on active testing of the subject according to an example embodiment.

FIG. 2 illustrates an example method for assessing the axial motor function of a muscular disability, in particular SMA in a subject based on active testing of the subject using the example device 105 of FIG. 1. While FIG. 2 is described with reference to FIG. 1, it should be noted that the method steps of FIG. 2 may be performed by other systems. The method includes prompting the subject to perform one or more diagnostic tasks (205). The method includes receiving, in response to the subject performing the one or more tasks, a plurality of sensor data via the one or more sensors (step 210). The method includes extracting, from the received sensor data, a plurality of features associated with the axial motor function of a muscular disability, in particular SMA (215). The method includes determining an assessment of the axial motor function of a muscular disability, in particular SMA, based on at least the extracted sensor data (step 220).

FIG. 2 sets forth an example method for assessing the axial motor function of a muscular disability, in particular SMA, based on active testing of the subject 110 using the example device 105 in FIG. 1. In some embodiments, active testing of the subject 110 using the device 105 may be selected via the user interface of the symptom monitoring application 130.

The method begins by proceeding to step 205, which includes prompting the subject to perform the diagnostic task. The device 105 prompts the subject 110 to perform one or more diagnostic tasks. In some embodiments, prompting the subject to perform the one or more diagnostic tasks includes prompting the subject to perform one or more actions. In some embodiments, the diagnostic tasks are anchored in or modelled after well-established methods and standardized tests for evaluating and assessing a muscular disability, in particular SMA.

In some embodiments, the diagnostic tasks may include to draw a shape as fast and accurate as possible.

The term "Test" as used herein describe a test where a subject is asked to perform the diagnostic task as described herein.

The method proceeds to step 210, which includes in response to the subject performing the one or more diagnostics tasks, receiving, a plurality of second sensor data via the one or more sensors. In response to the subject 110 performing the one or more diagnostic tasks, the diagnostic device 105 receives, a plurality of sensor data via the one or more sensors associated with the device 105. As mentioned above, the sensors associated with the device 105 include a first sensor 120a that is disposed within the device 105 and a second sensor 120b that is disposed within another device configured to be worn by the subject 110. The device 105 receives a plurality of first sensor data via the first sensor 120a and a plurality of second sensor data via the second sensor 120b.

The method proceeds to step 215, including extracting, from the received sensor data, a second plurality of features associated with the axial motor function of a muscular disability, in particular SMA. The device 105 extracts, from the received first sensor data and second sensor data, features associated with the axial motor function of a muscular disability, in particular SMA in the subject 110. The symptoms of a muscular disability, in particular SMA in the subject 110 may include a symptom indicative of the axial motor function of the subject 110. In some embodiments, the extracted features of the plurality of first and second sensor data may be indicative of symptoms of a muscular disability, in particular SMA such as the axial motor function.

The method proceeds to step 220, which includes determining an assessment of the axial motor function of a muscular disability, in particular SMA based on at least the extracted sensor data. The device 105 determines an assessment of the axial motor function of a muscular disability, in particular SMA in the subject 110 based on the extracted features of the received first and second sensor data. In some embodiments, the device 105 may send the extracted features over a network 180 to a server 150. The server 150 includes at least one processor 155 and a memory 160 storing computer-instructions for a symptom assessment application 170 that, when executed by the processor 155, determine an assessment of the axial motor function of a muscular disability, in particular SMA in the subject 110 based on the extracted features received by the server 150 from the device 105. In some embodiments, the symptom assessment application 170 may determine an assessment of the axial motor function of a muscular disability, in particular SMA, in the subject 110 based on the extracted features of sensor data received from the device 105 and a subject database 175 stored in the memory 160. The subject database 175 may include various clinical data. In some embodiments, the second device may be one or more wearable sensors. In some embodiments, the second device may be any device that includes a motion sensor with an inertial measurement unit (IMU). In some embodiments, the second device may include several devices or sensors. In some embodiments, the subject database 175 may be independent of the server 150. In some embodiments, the server 150 sends the determined assessment of the axial motor function of a muscular disability, in particular SMA in the subject 110 to the device 105. In some embodiments, such as in FIG. 1, the device 105 may output an assessment of the axial motor function of a muscular disability, in particular SMA on the display 160 of the device 105.

As discussed above, assessments of symptom severity and progression of a muscular disability, in particular SMA using diagnostics according to the present disclosure correlate sufficiently with the assessments based on clinical results and may thus replace clinical subject monitoring and testing. Diagnostics according to the present disclosure were studied in a group of subject with a muscular disability, in particular SMA subjects. The subjects were provided with a smartphone application that included an axial motor function test, in particular a test called "Walk the rope".

Figure 3:
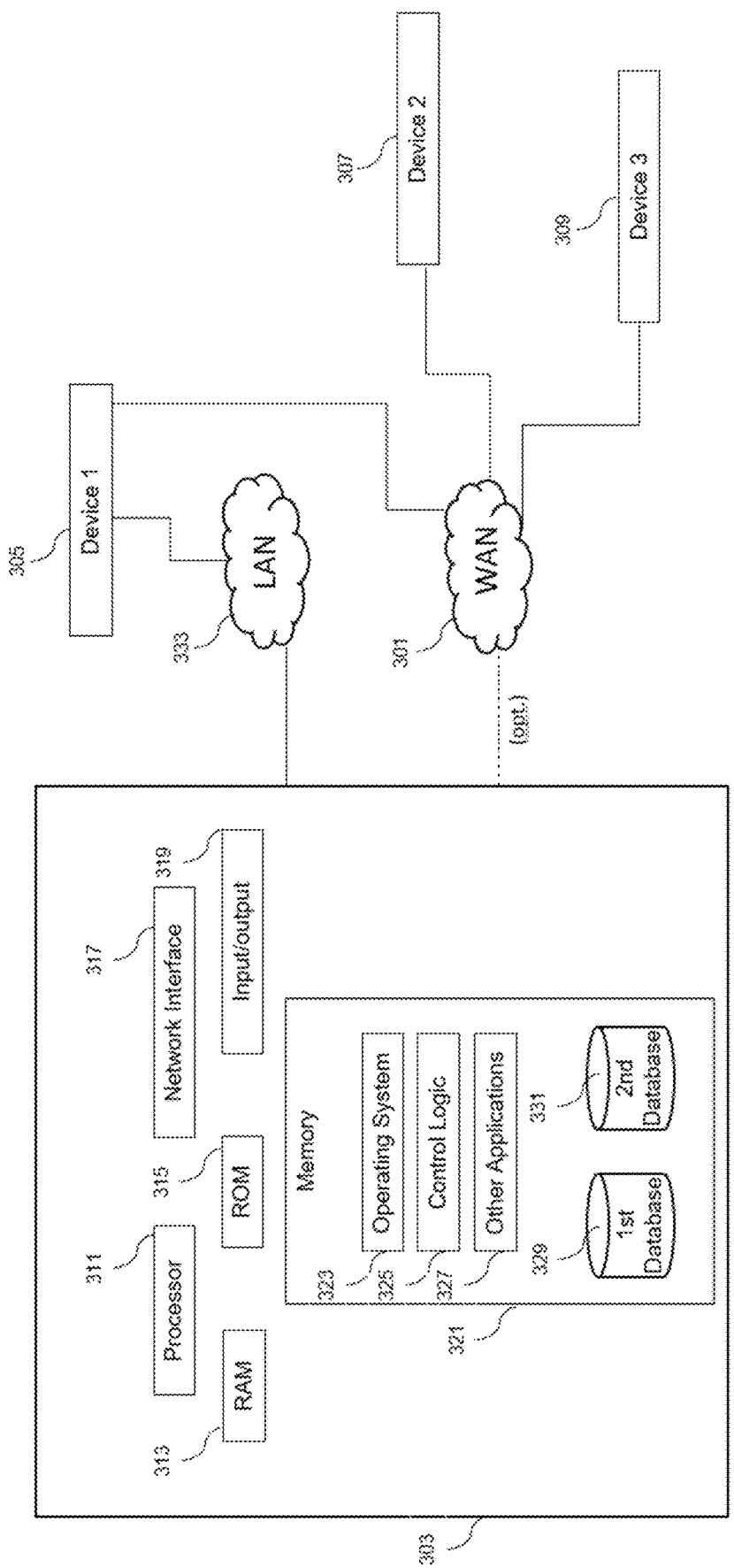
FIG. 3 illustrates one example of a network architecture and data processing device that may be used to implement one or more illustrative aspects described herein.

FIG. 3 illustrates one example of a network architecture and data processing device that may be used to implement one or more illustrative aspects described herein, such as the aspects described in FIGS. 1 and 2. Various network nodes 303, 305, 307, and 309 may be interconnected via a wide area network (WAN) 301, such as the Internet. Other networks may also or alternatively be used, including private intranets, corporate networks, LANs, wireless networks, personal networks (PAN), and the like. Network 301 is for illustration purposes and may be replaced with fewer or additional computer networks. A local area network (LAN) may have one or more of any known LAN topology and may use one or more of a variety of different protocols, such as Ethernet. Devices 303, 305, 307, 309 and other devices (not shown) may be connected to one or more of the networks via twisted pair wires, coaxial cable, fiber optics, radio waves or other communication media.

The term "network" as used herein and depicted in the drawings refers not only to systems in which remote storage devices are coupled together via one or more communication paths, but also to stand-alone devices that may be coupled, from time to time, to such systems that have storage capability. Consequently, the term "network" includes not only a "physical network" but also a "content network," which is comprised of the data—attributable to a single entity—which resides across all physical networks.

The components may include data server 303, web server 305, and client computers 307, 309. Data server 303 provides overall access, control and administration of databases and control software for performing one or more illustrative aspects described herein. Data server 303 may be connected to web server 305 through which users interact with and obtain data as requested. Alternatively, data server 303 may act as a web server itself and be directly connected to the Internet. Data server 303 may be connected to web server 305 through the network 301 (e.g., the Internet), via direct or indirect connection, or via some other network. Users may interact with the data server 303 using remote computers 307, 309, e.g., using a web browser to connect to the data server 303 via one or more externally exposed web sites hosted by web server 305. Client computers 307, 309 may be used in concert with data server 303 to access data stored therein, or may be used for other purposes. For example, from client device 307 a user may access web server 305 using an Internet browser, as is known in the art, or by executing a software application that communicates with web server 305 and/or data server 303 over a computer network (such as the Internet). In some embodiments, the client computer 307 may be a smartphone, smartwatch or other mobile computing device, and may implement a diagnostic device, such as the device 105 shown in FIG. 1. In some embodiments, the data server 303 may implement a server, such as the server 150 shown in FIG. 1.

Servers and applications may be combined on the same physical machines, and retain separate virtual or logical addresses, or may reside on separate physical machines. FIG. 1 illustrates just one example of a network architecture that may be used, and those of skill in the art will appreciate that the specific network architecture and data processing devices used may vary, and are secondary to the functionality that they provide, as further described herein. For example, services provided by web server 305 and data server 303 may be combined on a single server.

Each component 303, 305, 307, 309 may be any type of known computer, server, or data processing device. Data server 303, e.g., may include a processor 311 controlling overall operation of the rate server 303. Data server 303 may further include RAM 313, ROM 315, network interface 317, input/output interfaces 319 (e.g., keyboard, mouse, display, printer, etc.), and memory 321. I/O 319 may include a variety of interface units and drives for reading, writing, displaying, and/or printing data or files. Memory 321 may further store operating system software 323 for controlling overall operation of the data processing device 303, control logic 325 for instructing data server 303 to perform aspects described herein, and other application software 327 providing secondary, support, and/or other functionality which may or may not be used in conjunction with other aspects described herein. The control logic may also be referred to herein as the data server software 325. Functionality of the data server software may refer to operations or decisions made automatically based on rules coded into the control logic, made manually by a user providing input into the system, and/or a combination of automatic processing based on user input (e.g., queries, data updates, etc.).

Memory 321 may also store data used in performance of one or more aspects described herein, including a first database 329 and a second database 331. In some embodiments, the first database may include the second database (e.g., as a separate table, report, etc.). That is, the information can be stored in a single database, or separated into different logical, virtual, or physical databases, depending on system design. Devices 305, 307, 309 may have similar or different architecture as described with respect to device 303. Those of skill in the art will appreciate that the functionality of data processing device 303 (or device 305, 307, 309) as described herein may be spread across multiple data processing devices, for example, to distribute processing load across multiple computers, to segregate transactions based on geographic location, user access level, quality of service (QoS), etc.

One or more aspects described herein may be embodied in computer-usable or readable data and/or computer-executable instructions, such as in one or more program modules, executed by one or more computers or other devices as described herein. Generally, program modules include routines, programs, objects, components, data structures, etc. that perform particular tasks or implement particular abstract data types when executed by a processor in a computer or other device. The modules may be written in a source code programming language that is subsequently compiled for execution, or may be written in a scripting language such as (but not limited to) HTML or XML. The computer executable instructions may be stored on a computer readable medium such as a hard disk, optical disk, removable storage media, solid state memory, RAM, etc. As will be appreciated by one of skill in the art, the functionality of the program modules may be combined or distributed as desired in various embodiments. In addition, the functionality may be embodied in whole or in part in firmware or hardware equivalents such as integrated circuits, field programmable gate arrays (FPGA), and the like. Particular data structures may be used to more effectively implement one or more aspects, and such data structures are contemplated within the scope of computer executable instructions and computer-usable data described herein.

Figure 4:
FIG. 4 depicts an example illustrating the diagnostic application according to one or more illustrative aspects described herein.

FIG. 4 depicts an example illustrating the diagnostic test according to one or more illustrative aspects described herein. The user needs to select "Start" to begin with the task.

Figure 5:
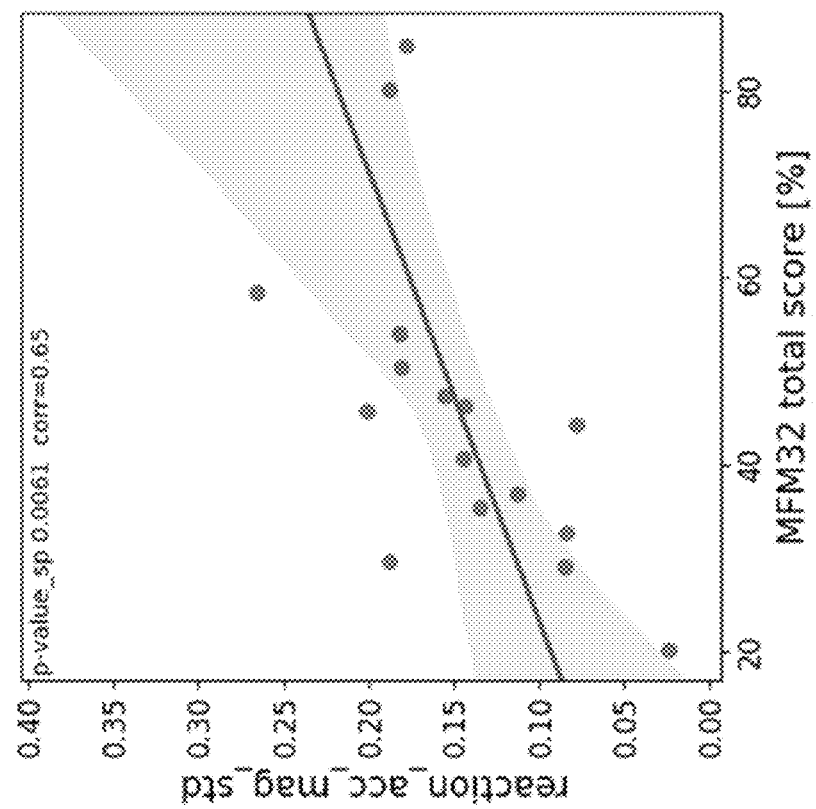
FIG. 5 are plots illustrating the sensor feature results according to example 1.
Figure 5:
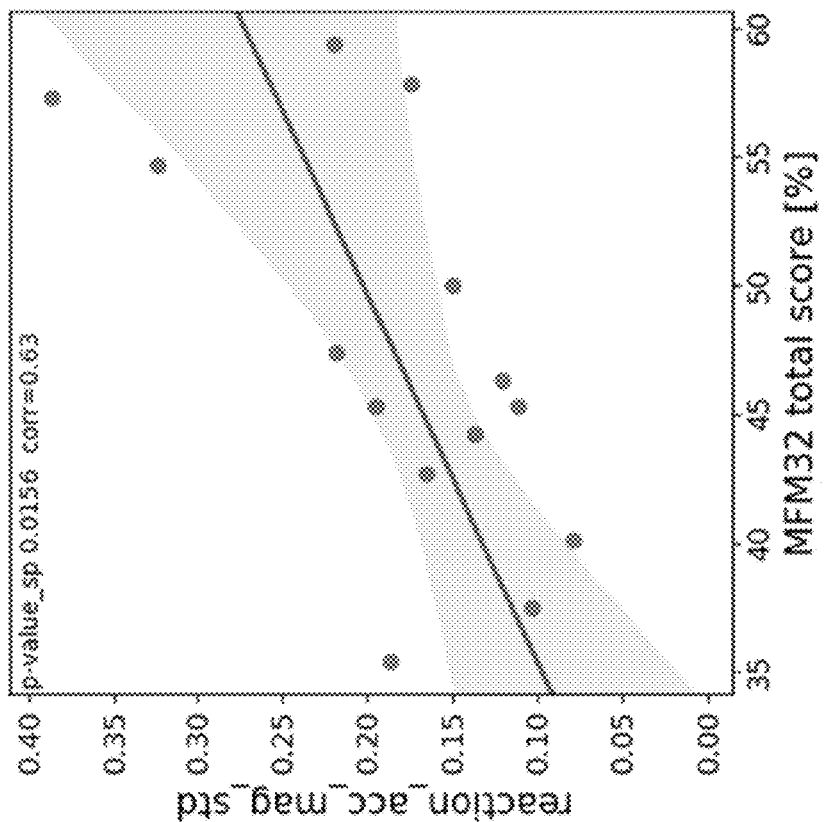

FIG. 5 are plots illustrating the sensor feature results according to the example "Walk the rope" diagnostic test depicted in FIG. 4. Sensor feature (standard deviation of acceleration magnitude to wind reaction) results are in agreement with clinical anchor (MFM32) in both studies.

Although the subject matter has been described in language specific to structural features and/or methodological acts, it is to be understood that the subject matter defined in the appended claims is not necessarily limited to the specific features or acts described above. Rather, the specific features and acts described above are disclosed as illustrative forms of implementing the claims.

Example 1

Characteristics of the analyzed cohort of patients, collected in two different studies.

i) OLEOS Study (clinicaltrials.gov/ct2/show/NCT02628743)

Participants analyzed: 20

Period for data analysis: smartphone data between last two clinical visits (176 days

|  | Mean (SD) | Range |
| --- | --- | --- |
| Age | 12.4 (4.1) [years] | 8.0 to 22.0 |
| Gender | 9 female, 11 male |  |
| FVC | 1.61 (0.87) [liter] | 0.33 to 3.10 | ii) JEWELFISH Study (clinicaltrials.gov/ct2/show/NCT03032172?term=BP39054)

Participants analyzed: 19

|  | Mean (SD) | Range |
| --- | --- | --- |
| Age | 23.2 (17.2) [years] | 6.0 to 60.0 |
| Gender | 6 female, 13 male |  |

Dataset acquisition using a computer-implemented test for determining by measuring variability of the acceleration occurring when turning the phone while reacting/compensating for sudden wind movements (Test: Walk the rope), an axial motor function test

| feature |  | Spearman correlation OLEOS | Spearman correlation Jewelfish | P-values OLEOS | P-value Jewelfish | N OLEOS | ICC OLEOS | N ICC OLEOS |
| --- | --- | --- | --- | --- | --- | --- | --- | --- |
| reaction_acc_mag_stn | Standard deviation of acceleration magnitude to wind reaction | −0.593 | −0.785 | 0.025 | 0 | 14 | 0.899 | 12 |
| reaction_acc_mag_stn | Standard deviation of acceleration magnitude to wind reaction | −0.613 | −0.768 | 0.02 | 0.001 | 14 | 0.899 | 12 |
| acc_mag_std_0_15 | Standard deviation of acceleration magnitude in 0-15 s | 0.637 | 0.734 | 0.014 | 0.001 | 14 | 0.825 | 12 |
| acc_mag_stn_0_15 | Standard deviation of acceleration magnitude in 0-15 s | −0.637 | −0.722 | 0.014 | 0.002 | 14 | 0.909 | 12 |
| acc_mag_std_0_15 | Standard deviation of acceleration magnitude in 0-15 s | 0.596 | 0.697 | 0.025 | 0.003 | 14 | 0.825 | 12 |
| gyr_x_std_15_30 | Gyroscop x-axis standard deviation in 15-30 s | −0.574 | −0.708 | 0.032 | 0.003 | 14 | 0.850 | 12 |
| acc_mag_stn_0_15 | Standard deviation of acceleration magnitude | −0.596 | −0.682 | 0.025 | 0.004 | 14 | 0.909 | 12 |

| feature | | Spearman correlation OLEOS | Spearman correlation Jewelfish | P-values OLEOS | P-value Jewelfish | N OLEOS | ICC OLEOS | N ICC OLEOS |
|---|---|---|---|---|---|---|---|---|
| | in 0-15 s | | | | | | | |
| reaction_acc_mag_std | Standard deviation of acceleration magnitude to wind reaction | 0.624 | 0.677 | 0.017 | 0.004 | 14 | 0.750 | 12 |
| reaction_acc_mag_std | Standard deviation of acceleration magnitude to wind reaction | 0.631 | 0.653 | 0.016 | 0.006 | 14 | 0.750 | 12 |
| gyr_z_stn_15_30 | Gyroscop z-axis standard deviation in 15-30 s | 0.833 | −0.620 | 0 | 0.014 | 14 | 0.705 | 12 |
| reaction_gyr_mag_median | Median of gyroscope magnitude to wind reaction | 0.713 | 0.584 | 0.004 | 0.017 | 14 | 0.708 | 12 |
| acc_z_stn_0_15 | Standard deviation of z-axis acceleration in 0-15 s | −0.661 | −0.562 | 0.01 | 0.023 | 14 | 0.891 | 12 |
| acc_z_stn_0_30 | Standard deviation of z-axis acceleration in 0-30s | −0.713 | −0.556 | 0.004 | 0.025 | 14 | 0.887 | 12 |
| mag_x_stn_15_30 | Standard deviation of x-axis magnetometer in 15-30 s | 0.691 | 0.521 | 0.006 | 0.047 | 14 | 0.936 | 12 |
| mag_mag_stn_15_30 | Standard deviation of magnitude magnetometer in 15-30 s | −0.644 | 0.516 | 0.013 | 0.049 | 14 | 0.809 | 12 |
| mag_mag_stn_15_30 | | 0.644 | −0.516 | 0.013 | 0.049 | 14 | 0.929 | 12 |

Covariate:
1: Total32 = MFM total score;
2: MFM_D2;
3: AGEIC;
4: MFM005;
5: MFM015
ICC: Intraclass Correlation Coefficient,
SD = standard deviation A test for was implemented on a mobile phone (iPhone); see FIG. 4. The patients shall balance a monster on a rope while wind is blowing the monster off balance. The phone should be held in both hands. The phone needs to be turned left and right to balance the monster. The phone can be rotated to further counter the effect of the wind. The patient shall indicate the position of the arm, i.e. outstretched, elbow bent but suspended, elbow resting on armrest or hand resting on table. The test lasts 30 seconds.

FIG. 5 shows the correlation of the clinical anchor test and the results from the walk the rope test (Standard deviation of acceleration magnitude to wind reaction in m/s$^2$). In the test when balancing the monster, their sometimes comes a wind challenge and this is the reaction in the first 2s after that and how much variability in the hand movements is happening. This is an average over all the wind challenge in one test run. The sensor feature results are in clear association with the clinical anchor (MFM32) in both studies.

The invention claimed is:

1. A diagnostic device for assessing an axial motor function of a subject with a muscular disability, the diagnostic device comprising:
   at least one processor;
   a plurality of first sensors being disposed within the diagnostic device; and
   memory storing computer-readable instructions that, when executed by the at least one processor, cause the at least one processor to at least:
      render a user interface on a display of the diagnostic device, the user interface comprising a prompt instructing the subject to perform a diagnostic task while interacting with diagnostic device, the diagnostic task comprising moving the diagnostic device to control a visual representation of an object balanced on another object while the object is subject to an emulated force trying to move the object off the other object;
      in response to the subject performing the diagnostic task, receive a plurality of sensor data from the plurality of first sensors disposed within the diagnostic device and at least one sensor being disposed within a second device configured to be worn by the subject and being in data communication with the diagnostic device, the sensor data corresponding to measurements of movements of the diagnostic device and the second device;
      extract, from the received plurality of sensor data, a plurality of features associated with the axial motor function of the subject with the muscular disability, at least one feature of the plurality of features corresponds to acceleration variability measurements associated with the movements of the at least one of the diagnostic device and the second device; and
      determine an assessment of the axial motor function of the subject based at least in part on an analysis of the extracted first plurality of features relative to the emulated force.

2. The diagnostic device of claim 1, wherein the diagnostic task further comprises keeping the object balanced on the other object for thirty seconds.

3. The diagnostic device of claim 1, wherein the diagnostic device is a smartphone.

4. The diagnostic device of claim 1, wherein the diagnostic task is associated with at least one of a motor function test.

5. A method assessing a muscular disability in a subject, the method comprising:
- determining a usage behavior parameter from a dataset comprising usage data for the diagnostic device according to claim 1 within a first predefined time window wherein the diagnostic device has been used by the subject; and
- comparing the determined at least one usage behavior parameter to a reference, whereby the subject with the muscular disability will be assessed.

6. A computer-implemented method for assessing an axial motor function of a subject with a muscular disability the method comprising:
- rendering a user interface on a display of a diagnostic device, the user interface comprising a prompt instructing the subject to perform a diagnostic task while interacting with diagnostic device, the diagnostic task comprising moving the diagnostic device to control a visual representation of an object balanced on another object while the object is subject to an emulated force trying to move the object off the other object;
- in response to the subject performing the diagnostic task, receiving a plurality of sensor data via a plurality of sensors associated with a device, a first sensor being disposed within the diagnostic device, and a second sensor being disposed within a wearable device being worn by the subject during the performance of the diagnostic task, the second sensor being in data communication with the diagnostic device, and the sensor data corresponding to measurements of movements of the diagnostic device and wearable device;
- extracting, from the sensor data, a plurality of features associated with the axial motor function of the subject with the muscular disability, at least one feature of the plurality of features corresponds to acceleration variability measurements associated with the movements of the at least one of the diagnostic device and the wearable device; and
- determining a first an assessment of the axial motor function of the subject with the muscular disability based at least in part on the extracted plurality of features and the emulated force.

7. The computer-implemented method of claim 6, wherein the axial motor function of the subject is assessed based on, and the subject keeping the object balanced on the other object for thirty seconds.

8. The computer-implemented method of claim 6, wherein the subject is human.

9. A non-transitory machine readable storage medium comprising machine-readable instructions, that when executed by a processor of a diagnostic device cause the processor to at least:
- render a user interface on a display of the diagnostic device; the user interface comprising a prompt instructing the subject to perform a diagnostic task while interacting with diagnostic device, the diagnostic task moving the diagnostic device to keep the object balanced on the other object for thirty seconds while the object is subject to an emulated force applied to the object causing the object to move off of the other object;
- in response to the subject performing the diagnostic task, receive a plurality of sensor data via one or more sensors associated with a device, a first sensor being disposed within the diagnostic device, and a second sensor being disposed within a wearable device being worn by the subject during the performance of the diagnostic task, the second sensor being in data communication with the diagnostic device, and the sensor data corresponding to measurements of movements of the diagnostic device and wearable device;
- extract, from the received sensor data, a plurality of features associated with an axial motor function of the subject with the muscular disability, at least one feature of the plurality of features corresponds to acceleration variability measurements associated with the movements of the at least one of the diagnostic device and the wearable device; and
- determine an assessment of the axial motor function of the subject with the muscular disability based at least in part on the extracted plurality of features and the emulated force.

10. A method, comprising;
- prompting a subject to perform a diagnostic test by interacting with a diagnostic device for a predefined period of time, the diagnostic device rendering a user interface comprising a first object balancing a second object, movements of the diagnostic device by the subject causing the first object to remain balanced on the second object when the first object is subject to an emulated force;
- scoring the subject on the performance of the diagnostic task;
- assigning the subject for a muscular disability by comparing the determined score to a reference; and
- administering a pharmaceutically active agent to the subject to decrease likelihood of progression of the muscular disability.

11. The method of claim 10, wherein the pharmaceutically active agent is suitable to treat the muscular disability in the subject, and the pharmaceutically active agent comprises Nusinersen, Onasemnogene abeparvovec, Risdiplam or Branaplam.

12. The method according to claim 10, whereby at least one parameter is determined after administration of the pharmaceutically active agent and is compared to the reference of the subject before the subject received treatment with the pharmaceutical active agent.

13. The method according to claim 10, whereby the subject is human.

14. The method according to claim 10, whereby the pharmaceutically active agent is Risdiplam.

* * * * *